United States Patent [19]

Cornils et al.

[11] Patent Number: 4,616,096

[45] Date of Patent: Oct. 7, 1986

[54] PROCESS FOR THE PRODUCTION OF ALDEHYDES

[75] Inventors: Boy Cornils, Dinslaken; Helmut Bahrmann, Brunen; Wolfgang Lipps, Isny; Werner Konkol, Oberhausen, all of Fed. Rep. of Germany

[73] Assignee: Ruhrchemie Aktiengesellschaft, Fed. Rep. of Germany

[21] Appl. No.: 770,732

[22] Filed: Aug. 29, 1985

[30] Foreign Application Priority Data

Aug. 30, 1984 [DE] Fed. Rep. of Germany ....... 3431840

[51] Int. Cl.$^4$ ............................................. C07C 45/50
[52] U.S. Cl. ..................................... 568/454; 568/451
[58] Field of Search ............................... 568/451, 454

[56] References Cited

U.S. PATENT DOCUMENTS

| Re. 31,812 | 1/1985 | Kuntz | 568/454 |
| 4,248,802 | 2/1981 | Kuntz | 568/454 |
| 4,258,215 | 3/1981 | Dawes | 568/454 |
| 4,306,084 | 12/1981 | Petit | 568/454 |
| 4,399,312 | 8/1983 | Russell et al. | 568/454 |

FOREIGN PATENT DOCUMENTS

| 007609 | 2/1980 | European Pat. Off. | 568/454 |
| 41805 | 4/1975 | Japan | 568/454 |

Primary Examiner—Werren B. Lone
Attorney, Agent, or Firm—Jordan B. Bierman

[57] ABSTRACT

A method for the production of aldehydes from olefins with $CO/H_2$ in the presence of a water-soluble rhodium-containing catalyst system is described. The reaction proceeds at 0.1 to 10 MPa and 20 to 160° C. Ultrasound acts on the reaction mixture, consisting of an aqueous catalyst, an olefin, synthesis gas and the end products.

14 Claims, No Drawings

PROCESS FOR THE PRODUCTION OF ALDEHYDES

The present invention relates to a process for the production of aldehydes by hydroformylation of olefins in the presence of water-soluble rhodium complex catalysts.

The production of aldehydes and alcohols by reaction of olefins with carbon monoxide and hydrogen is known. The reaction is catalyzed by hydridometal carbonyls, preferably those of the metals of Group 8 of the Periodic Table. Besides cobalt, which is widely used as a catalyst metal, rhodium is becoming increasingly important. In contrast to cobalt, rhodium permits conduction of the reaction at low pressure; moreover, primarily straight-chain n-aldehydes and only a minor amuont of iso-aldehydes is formed. Lastly, the hydrogenation of the olefins to undesired saturated hydrocarbons is clearly lower when using rhodium catalysts than when using cobalt catalysts.

In the known industrial process, the rhodium catalyst is employed in the form of modified hydridorhodium carbonyls, preferably containing additional ligands, which carbonyls may advantageously be present in excess. As ligands, tertiary phosphines or phosphites have proven especially successful. Their use makes it possible to lower the reaction pressure to values below 300 bars (30 Mpa).

In this process, however, the separation of the reaction products and the recovery of the catalysts homogeneously dissolved in the reaction product present problems. For this purpose the reaction product is generally distilled from the reaction mixture but, because of the thermal sensitivity of the formed aldehydes and alcohols, this method can be adapted in practice only for the hydroformylation of low olefins; i.e. olefins with up to about 5 carbon atoms in the molecule. Also, it has been found that the thermal stress on the distillation material leads to considerable loss of catalyst by decomposition of the rhodium complex compounds.

The described shortcomings are avoided by the use of catalyst systems which are soluble in water. Such catalysts are described, for example, in DE-PS No. 26 27 354. The solubility of the rhodium complex compounds is achieved by using sulfonated triaryl phosphines as the complex constituent. The separation of the catalyst from the reaction product after the completion of the hydroformylation reaction is achieved simply by splitting of the aqueous and organic phases; i.e. without distallation, and hence without additional thermal process steps. Besides sulfonated triaryl phosphines, as complex constituents of water-soluble rhodium complex compounds, carboxylated triaryl phosphines are used.

The reaction of the olefin with carbon monoxide and hydrogen proceeds in the aqueous phase containing the catalyst. While this process converts the lower olefins (such as ethylene and propylene) in yields as high as in the known processes, when higher olefins are used they decrease noticeably. For example, 1-hexene or 1-decene reacts only to an unsatisfactory degree.

Presumably, this problem arises because the solubility—and hence the concentration—of the olefins in the aqueous phase decreases with increasing number of carbon atoms. Greater intensity of agitation for better distribution of the olefin in the aqueous phase increases the conversion only slightly.

In Nachr. Chem. Techn. Lab. 31 (1983) 10,798 ff, the use of ultrasound in organic synthesis is reported. Ultrasound accelerates heterogenous reactions, in particular those in which solids and liquids are involved. Among the examples are named the partial reduction of symmetrical or unsymmetrical $\alpha$, -$\alpha$ dibromoketones by means of mercury, the two-phase saponification of esters, the formation of organolithium and Grignard compounds, and the synthesis of lithium organocuprates. The use of ultrasound in three-phase systems in which a gaseous phase is also involved is not discussed.

The task was to develop a process which permits the formation of aldehydes from olefins, in particular those with up to 20 carbon atoms, preferably with 4 to 20 carbon atoms, by hydroformylation. At the same time, a high conversion of the starting olefin to the desired end product per unit at a given catalyst quantity should be obtained.

The above objectives are achieved by a process for the production of aldehydes with 3 to 21 carbon atoms with carbon monoxide and hydrogen in the presence of water and a water-soluble, rhodium-containing complex compound as the catalyst. The reaction is carried out at temperatures of 20° to 160° C. and pressures of 0.1 to 10 Mpa. There is 0.1 to 15 mmol of the water-soluble rhodium complex compound per kilogram of the aqueous phase and the volumetric ratio of aqueous to organic phase is 1:100 to 100:1. The reaction mixture is subjected to ultrasound and optionally agitated.

Although it might be expected that the action of ultrasound on the reaction system would produce intensive homogenization of the liquid reagents, it was not to be foreseen that an increase in conversion would occur. It is known that the ultrasound reduces the solubility of gases in liquids and accelerates the degassing of liquids.

Furthermore, it must be noted that, when the ultrasound is used, shock waves occur in the micro regions, and these lead to very high pressures and temperatures. In view of the fact that it is known that the thermal stress during distillation leads to decomposition of the catalyst, it was to be expected that ultrasound would also bring about destruction of the catalyst.

The reaction of the starting materials takes place in a pressurized reactor of metal or glass equipped with an agitator. The reagents, i.e. olefin and synthesis gas, are supplied along with the aqueous catalyst solution jointly or separately. The use of distributing devices such as sieve bottoms or frits for the gaseous components has proved successful. It is also possible to combine agitation and distribution of the gaseous reactants, e.g. by using an aerator.

The term ultrasound is understood to refer to sound waves of a frequency of at least 20 kHz. Preferably, ultrasonic generators which emit a frequency of 20 to 60 kHz are used. However, it is also possible to use higher frequencies, for example 200 kHz, with good results.

As ultrasonic generators, commercial ultrasonic cleaning equipment has been found suitable. In this case, glass vessels are satisfactory as reactors. The transmission of the sound energy occurs through low-viscosity liquids. This type of process conduction, however, is limited to reactions at low pressures.

To carry out the reaction at higher pressures, appropriately dimensioned ultrasonic immersion oscillators are placed directly in the reaction vessel. This procedure has the advantage that the sound energy acts on the reaction mixture itself, so that the power losses, otherwise resulting from the use of transmitting liquids, do not occur. Immersion oscillators can be introduced in agitator autoclaves, relatively large agitator reactors, as well as in flow tubes.

The water-soluble catalysts used according to the invention are complex compounds of rhodium which contain, besides carbon monoxide and hydrogen, sulfonated or carboxylated phosphines. Preferred are sulfonated or carboxylated triaryl phosphines, in particular triphenyl phosphines or trinaphthyl phosphines. It is not necessary that all three aryl radicals carry sulfonic acid groups or carboxyl groups. It has been found that one sulfonic acid group or one carboxyl group in the phosphine molecule imparts sufficent water solubility to the complex compound. The catalyst may be added to the reaction mixture as a preform, or it may be formed in situ. It has been found especially desirable to charge the water-soluble phosphines in excess; preferably, 5 to 100 moles of phosphine per g-atom of rhodium.

The concentration of the rhodium complex compound used as a catalyst in the aqueous phase is 0.1–15 mmol and preferably 0.8–12 mmol per kg of aqueous phase. The volumetric ratio of aqueous to organic phase is 1:100 to 100:1; especially a ratio of 10:1 to 100:1 by volume. The conversion of the reagents occurs at 20°–160° C., preferably 80°–140° C., under pressures of 0.1 to 10 MPa, preferably 1–5 MPa. The synthetic gas used for the hydroformylation contains carbon monoxide and hydrogen approximately in a ratio of 1:1 by volume. However, it is also possible to vary this ratio and to use gas mixtures which are higher in carbon monoxide or in hydrogen.

The new procedure is especially suitable for the conversion of olefins with 2 to 20 carbon atoms to the aldehydes having one additional carbon atom. Examples of suitable olefins are butene, pentene, hexene, diisobutylene, tripropylene, decene, dicylopentadiene, undecene, dodecene, tetrapropylene, pinen, limonene, terpinene, camphene, oleic acid, oleic acid ester, elaidic acid and elaidic acid ester.

The invention is illustrated by a number of examples. As measure for the conversion, the Turn-Over Number (TON) is used. It is defined by the expression $$TON = \frac{\text{mmol aldehyde}}{\text{mg-atom Rh} \times t} \quad [1/\text{min}]$$

The abbreviation TPPTS stands for the sodium salt of triphenylphosphine trisulfonate.

EXAMPLE 1

Into a glass vessel is placed 0.218 mmol (400 mg) HRh(CO)(TPPTS)$_3$ dissolved in 200 ml water and 200 g n-hexene-1. The mixture is vigorously stirred, and 60 1/h of synthesis gas (CO:H$_2$=1:1) is passed therethrough at 300° C. and normal pressure for 7 hours. After gas chromotographic analysis, 6.29 mmol n-heptanal and 1.11 mmol 2-methyl hexanal are obtained. The TON is 0.08 min$^{-1}$.

EXAMPLE 2

The aqueous catalyst solution of Example 1 is recovered after separation of the organic phase and then is admixed with a new portion of 200 g n-hexene-1. Under the conditions of Example 1, but under action of ultrasound of a frequency of 35 kHz, 60 1/h of synthesis gas (CO:H$_2$=1:1) is passed through the mixture for 15 hours. After gas chromatographic analysis, 30.6 mmol n-heptanal and 5.4 mmol 2methyl hexanal are obtained.

The TON is 0.183 min$^{-1}$, an increase of 2.3-fold as compared with Example 1.

EXAMPLE 3 (Comparison test)

A glass autoclave is provided with an agitator, a temperature measuring device, and a sampling nipple. 0.33 mmol (600 mg) HRh(CO)(TPPTS)$_3$ dissolved in 180 g water is admixed with 200 g n-hexene-1. With synthesis gas (CO:H$_2$=1:1), which is replenished as it is consumed, a pressure of 1 MPa is maintained and the mixture is allowed to react under agitation (rotational speed: 500 rpm) at 35° C. for 3 hours. Gas chromatographic analysis (GC) of the organic layer indicates 30.3 mmol n-heptanal and 7.6 mmol 2-methyl hexanal are obtained. The TON is 0.637.

EXAMPLE 4

After separation of the organic layer mentioned in Example 3 the aqueous catalyst solution is admixed with 300 g n-hexene-1. Under the conditions of Example 3 the mixture is treated with ultrasound for a reaction time of 5 hours. The upper organic layer contains 115 mmol n-heptanal and 29 mmol 2-methyl hexanal, determined by GC. The TON is 1.45.

EXAMPLE 5 (Comparison test)

A 2-liter steel autoclave, provided with an agitator, a temperature measuring device, and a sampling nipple, contains two commercial immersion oscillators which generate 23 and 40 kHz ultrasound. Their power consumption is 300 watts each. The reactor is charged with 600 g n-hexene-1 and 2 mmol (3.674 g) HRh(CO)(TPPTS)$_3$ dissolved in 600 g water. With synthesis gas (CO:H$_2$=1:1), which is then replenished as it is consumed, a pressure of 1 MPa is maintained and the mixture is allowed to react for 5 hours under agitation (rotational speed 500 rpm) at 35° C. without the action of ultrasound. 389 mmol n-heptanal and 97 mmol 2-methyl-hexanal are obtained. The TON is 0.81.

EXAMPLE 6

The reaction mixture of Example 5 is further treated with ultrasound (power consumption of the immersion oscillators: 2×300 watts) for another 3 hours in the apparatus described in Example 5. With synthesis gas (CO:H$_2$=1:1). which is replenished as it is consumed, a pressure of 1 MPa is maintained and the mixture allowed to react under agitation (rotational speed: 500 rpm) at 35° C. The organic layer is separated and discharge. It contains an additional amount of 861 mmol n-heptanal and 189 mmol 2-methyl hexanal. The TON is 2.92.

EXAMPLE 7 (Comparison test)

The aqueous catalyst solution of Example 6 is mixed with 600 g n-hexene-1. With synthesis gas (CO:H$_2$=1:1), which is replenished as it is consumed, a pressure of 2.5 MPa is maintained and the mixture allowed to react under agitation (rotational speed: 500 rpm) at 35° C. for 3 hours. The organic layer contains 945 mmol n-heptanal and 222 mmol 2-methyl hexanal. The TON is 3.24.

EXAMPLE 8

The reaction mixture of Example 7 is further treated with ultrasound for 30 minutes under the conditions of Example 7. An additional 554 mmol n-heptanal and 136 mmol 2-methyl hexanal in the organic layer are obtained. The TON is 11.34. The organic upper layer is separated and discharged. The aqueous layer remains in the reactor.

EXAMPLE 9 (Comparison test)

The aqueous catalyst solution of Example 8 is mixed with 600 g n-hexene-1 and reacted in a manner similar to that of Example 7, except that the pressure is 5 MPa. The synthesis gas is $CO:H_2=1:1$. After a reaction time of one hour, 462 mmol n-heptanal and 102 mmol 2-methyl hexanal are obtained. The TON is 4.70.

EXAMPLE 10

The reaction mixture of Example 9, under the conditions of Example 9, is additionally treated with ultrasound for 30 minutes. An additional 722 mmol n-heptanal and 180 mmol 2-methyl hexanal are obtained. The TON is 5.04.

EXAMPLE 11 (Comparison test)

200 g diisobutylene and 0.330 mmol (600 mg) $HRh(CO)(TPPTS)_3$, dissolved in 200 g water, are placed in a glass autoclave. With synthesis gas ($CO:H_2=1:1$), which is replenished as it is consumed, a pressure of 1 MPa is maintained and the mixture allowed to react under agitation (rotational speed: 400 rpm) at 35° C. for 4 hours. Gas chromatography indicates no aldehydes were formed.

Under the same conditions, but with a rotational speed increased to 1900 rpm, the same mixture is reacted for another 4 hours. 0.053 mmol of $C_9$ aldehydes is obtained. The TON is $6.7 \times 10^{-4}$.

EXAMPLE 12 the reaction mixture of Example 11 is additionally treated with ultrasound under the conditions of Example 11 for 4 hours. An additional 0.76 mmol of $C_9$ aldehydes is obtained. The TON is $9.6 \times 10^{-3}$.

Preforming of an Rh-TPPTS solution with $CO/H_2$

In a 5-liter steel autoclave, 987 mmol (561 g) TPPTS, as well as 14.58 mmol (1.5 g Rh) rhodium acetate, dissolved in 3 kg water, are charged. This solution is treated for 3 hours at 125° C. with synthesis gas ($CO:H_2=1:1$) at a pressure of 2.5 MPa. The P:Rh ratio is 67:1. The solution contains 500 ppm rhodium and is used in Examples 13-16.

EXAMPLE 13 (Comparison test)

180 g of the preformed Rh-TPPTD catalyst solution and 200 g n-hexene-1 are placed in a glass autoclave. With synthesis gas ($CO:H_2=1:1$), which is replenished as it is consumed, a pressure of 1 MPa is maintained and the mixture allowed to react under agitation at 120° C. for 5 hours. There are obtained 111.4 mmol n-heptanal and 1.1 mmol 2-methyl hexanal. The TON is 0.43.

EXAMPLE 14

The reaction mixture of Example 13 is additionally treated with ultrasound under the conditions of Example 13. After a reaction time of 5 hours, an additional 279 mmol n-heptanal and 3 mmol 2-methyl hexanal are obtained. The Ton is 1.075.

EXAMPLE 15 (Comparison test)

In the steel autoclave of Example 5, which is equipped with two immersion oscillators, there are charged 600 g of the preformed Rh-TPPTS catalyst solution and 600 g n-hexene-1. With synthesis gas ($CO:H_2=1:1$), which is replenished as it is consumed, a pressure of 2.5 MPa is maintained and the mixture allowed to react under agitation for 3 hours at 120° C. There are obtained 114 mmol n-heptanal and 2 mmol 2-methyl hexanal. The TON is 0.74.

EXAMPLE 16

The reaction mixture of Example 15 is additionally treated with ultrasound (power consumption of the immersion oscillators $2 \times 300$ watts) under the conditions of Example 15 for 2 hours. There are obtained an additional 616 mmol n-heptanal and 6 mmol 2-methyl hexanal. The TON is 1.78.

What we claim is:

1. A process for the production of aldehydes having 3 to 21 carbon atoms comprising reacting olefins having 2 to 20 carbon atoms with carbon monoxide and hydrogen in the presence of water and a water-soluble rhodium complex, containing carbon monoxide, hydrogen, and sulfonated or carboxylated phosphines as a catalyst in a reaction mixture, thereby forming an organic phase and an aqueous phase, and subjecting said mixture to ultrasound of at least 20 kHz.

2. The process of claim 1 wherein the reaction is carried out at temperatures of 20° to 160° C. and pressures of 0.1 to 10 MPa, said aqueous phase containing 0.1 to 15 mmol of the water-soluble rhodium complex per kilogram of said aqueous phase, and the volumetric ratio of said aqueous phase to said organic phase being 1:100 to 100:1.

3. The process of claim 2 wherein said temperatures are 80° to 140° C.

4. The process of claim 2 wherein said pressures are 1 to 5 MPa.

5. The process of claim 2 wherein said volumetric ratio is 1:10 to 10:1.

6. The process of claim 2 wherein said aqueous phase contains 0.8 to 12.0 mmol of rhodium-containing complex per kg. of said aqueous phase.

7. The process of claim 2 wherein said mixture is agitated during said reaction.

8. The process of claim 3 wherein said pressures are 1 to 5 MPa.

9. The process of claim 3 wherein said volumetric ratio is 10:1 to 100:1.

10. The process of claim 4 wherein said volumetric ratio is 10:1 to 100:1.

11. The process of claim 3 wherein said aqueous phase contains 0.8 to 12.0 mmol of said complex per kilogram of said aqueous phase.

12. The process of claim 4 wherein said aqueous phase contains 0.8 to 12.0 mmol of said complex per kilogram of said aqueous phase.

13. The process of claim 5 wherein said aqueous phase contains 0.8 12.0 mmol of said complex per kilogram of said aqueous phase.

14. A process for the production of aldehydes having 3 to 21 carbon atoms comprising reacting olefins having 2 to 20 carbon atoms with carbon monoxide and hydrogen in the presence of water and a water-soluble rhodium complex as a catalyst in a reaction mixture, thereby forming an organic phase and an aqueous phase, and subjecting said mixture to ultrasound of at least 20 kHz.

* * * * *